(12) United States Patent
Galperin et al.

(10) Patent No.: US 7,449,597 B1
(45) Date of Patent: Nov. 11, 2008

(54) HOMOGENEOUS CARBONYLATION CATALYST AND PROCESS USING THE CATALYST

(75) Inventors: Leonid B. Galperin, deceased, late of Wilmette IL (US); by Irina Galperin, legal representative, Wilmette, IL (US); Paul T. Barger, Arlington Heights, IL (US); Robert H. Jensen, Hinsdale, IL (US); Albert L. Lapidus, Moscow (RU); Oleg L. Eliseev, Lubertsy (RU)

(73) Assignee: UOP LLC, Des Plaines, IL (US)

( * ) Notice: Subject to any disclaimer, the term of this patent is extended or adjusted under 35 U.S.C. 154(b) by 327 days.

(21) Appl. No.: 10/968,537

(22) Filed: Oct. 19, 2004

(51) Int. Cl.
C07C 51/14 (2006.01)
(52) U.S. Cl. ...................... 562/522; 562/521
(58) Field of Classification Search .............. 560/517, 560/521, 206, 232; 502/150, 162, 167, 224, 502/230, 327
See application file for complete search history.

(56) References Cited

U.S. PATENT DOCUMENTS

| | | | |
|---|---|---|---|
| 4,739,110 A * | 4/1988 | Drent | 560/207 |
| 4,960,926 A | 10/1990 | Drent | 560/233 |
| 5,254,720 A | 10/1993 | Wu | 560/105 |
| 5,731,255 A | 3/1998 | Pan et al. | 502/155 |
| 5,760,284 A * | 6/1998 | Zoeller | 560/233 |
| 5,866,716 A | 2/1999 | Schäfer et al. | 562/522 |
| 5,869,738 A | 2/1999 | Pan et al. | 560/207 |
| 6,646,159 B2 | 11/2003 | Baird et al. | 562/521 |
| 2002/0019562 A1 * | 2/2002 | Baird et al. | 560/241 |

FOREIGN PATENT DOCUMENTS

JP 63230653 * 9/1988

OTHER PUBLICATIONS

Danilczuk, Polish Journal of Chemistry (1984), 58(4-5-6), 345-54.*
J. Org. Chem., vol. 38 (1973), No. 18 p. 3192.
Journal of Organometallic Chemistry, 455 (1993), 247-253.

* cited by examiner

Primary Examiner—Karl J Puttlitz
(74) Attorney, Agent, or Firm—Frank S Molinaro

(57) ABSTRACT

A catalyst useful for carbonylation of olefins has been developed. The catalyst comprises a palladium compound, e.g. $PdIm_4Cl_2$, where Im is imidazole and HCl dissolved in water or an alcohol. Carbonylation using this catalyst involves contacting an olefin stream preferably in a solvent such as o-xylene with the catalyst and carbon monoxide at carbonylation conditions to provide a carboxylic acid or an ester. When the catalyst solvent is water one can obtain an acid as the product, but when the catalyst solvent is an alcohol one obtains an ester as the product.

9 Claims, No Drawings

US 7,449,597 B1

HOMOGENEOUS CARBONYLATION CATALYST AND PROCESS USING THE CATALYST

FIELD OF THE INVENTION

This invention relates to a catalyst useful for the carbonylation of olefinic hydrocarbons. The catalyst comprises a palladium triphenylphosphine or palladium imidazole complex, HCl and a solvent such as water or alcohols. This invention also relates to a process for carbonylating olefins to oxygenated products such as carboxylic acids using the catalyst.

BACKGROUND OF THE INVENTION

Carbonylation of olefins to produce oxygenated products such as esters, acids, etc. is a well known process and one which is practiced commercially for the production of low molecular weight acids such as acetic acid.

Carbonylation catalysts are also known in the art as shown by an article in *J. Org. Chem.*, Vol. 38 (1973), No. 18 p. 3192 which describes studies of the effect of several variables on a palladium-phosphine catalyst for use in carbonylation. Some of the variables studied were temperature, reagents, solvents and phosphine substituents. Another article by J. F. Knifton in *J. Org. Chem., Vol* 41, (1976), No. 17 p. 2885 describes the production of carboxylic acid esters from linear α-olefins using a ligand-stabilized platinum(II)-group 4B metal halide catalyst exemplified by $[(C_6H_5)_3P]_2PdCl_2$—$SnCl_2$. This reference reports the result of using a variety of palladium complexes and reported the performance of the catalyst system varied with the coordinated ligands. The reference also indicates that internal, disubstituted olefins carbonylate more slowly than linear olefins and produce a different product distribution.

Hoffman et al. in *Ind. Eng. Chem. Prod Res. Dev.,* 1980, 19, 330-334 describes the examination of 300 combinations of nonnoble group VIII metals and halogen-free promoters as catalysts for carbonylation. An apparent optimum catalyst system of cobalt/pyridine or γ-picoline and α-octene was used to study the effect of various parameters on the carbonylation of a mixture of isomeric internal n-dodecenes. This reference describes the use of hydroformylation to produce fatty acids and "fatty type" alcohols and indicates carbonylation had not yet been used to produce fatty acid esters or alcohols commercially.

U.S. Pat. No. 4,960,926 describes a catalyst system for carbonylation comprising a palladium compound such as palladium acetate, an organic phosphine, a non-carboxylic or non-halogen acid with a pKa of <2, a promoter and a catalyst stabilizer. The reference indicates the unsaturated compounds in the feed stream which are converted in the reaction can be cycloalkenes. An article in *Journal of Organometallic Chemistry,* 455 (1993), 247-253, describes the effects of different ligand structures and acid types in what appears to be a similar catalyst system.

U.S. Pat. No. 5,254,720 describes a process for producing aliphatic carboxylic acids or their alkyl esters using a catalyst system comprising palladium and copper compounds, at least one acid stable ligand, and an acid such as hydrochloric acid. This reference also indicates an optional solvent may be present in the reaction zone and lists as possible solvents a variety of ketones including acetone and aromatic hydrocarbons including xylenes. U.S. Pat. No. 5,869,738 issued to L. R. Pan et al. describes another carbonylation catalyst system comprising a Group VIII metal such as palladium or palladium chloride supported on a carrier, a ligand such as triphenylphosphine and an acid such as an alkyl sulfonic acid. The reaction may be carried out in an inert organic solvent. Mentioned solvents include an aliphatic hydrocarbon e.g. octane, an aromatic hydrocarbon such as benzene or a halogenated hydrocarbon such as chloroform or a mixture of these.

U.S. Pat. No. 5,866,716 discloses a halogen-free catalyst system consisting of a rhodium compound and at least one nitrogen containing heterocyclic compound. A large number of heterocyclic compounds are enumerated including pyridines, quinolines and imidazoles. Finally, U.S. Pat. No. 5,731,255 discloses a carbonylation catalyst system, a Group VIII metal sources, a ligand such as triphenylphosphine and an acid such as alkyl-sulfonic acid.

U.S. Pat. No. 6,646,159 B2 discloses a process for preparing alcohols and acids from paraffins. The catalyst used in the process is a palladium compound plus a LiI promoter and an organic acid such as formic acid.

In contrast to this art, applicants have developed a carbonylation catalyst comprising a palladium triphenylphosphine or a palladium imidazole complex in combination with HCl and a solvent selected from water, an alcohol and mixtures thereof. The advantages to this catalyst is that because it does not use promoters such as iodide compounds in conjunction with acids such as formic acid, one can use stainless steel to fabricate the reactors instead of more costly zirconium.

SUMMARY OF THE INVENTION

As stated, one embodiment of the invention is a homogeneous catalyst for the carbonylation of olefinic hydrocarbons consisting essentially of a palladium compound selected from the group consisting of $PdCl_2$ $(PPh_3)_2$, $PdIm_4Cl_2$ and mixtures thereof, where Im is imidazole or a substituted imidazole, HCl and a solvent selected from the group consisting of water, alcohols and mixtures thereof.

Another embodiment of the invention is a process for preparing oxygenated hydrocarbons comprising contacting a feedstream comprising a mixture of paraffinic olefinic hydrocarbons with carbon monoxide and a homogeneous catalyst at carbonylation conditions, thereby converting at least a portion of the olefinic hydrocarbons to oxygenated products and where the homogeneous catalyst comprises a palladium compound selected from the group consisting of $PdCl_2$ $(PPh_3)_2$, $PdIm_4Cl_2$ and mixtures thereof, where Im is imidazole or a substituted imidazole, HCl and a solvent selected from the group consisting of water, alcohols and mixtures thereof.

Additional objects, embodiments and details of this invention can be obtained from the following detailed description of the invention.

DETAILED DESCRIPTION OF THE INVENTION

As stated this invention relates to a homogeneous catalyst and an olefin carbonylation process using the catalyst. One essential element of the catalyst of the invention is a palladium compound selected from a palladium phosphine complex or a palladium imidazole complex. Although any palladium triphenylphosphine complex can be used, a preferred complex is dichlorobis (triphenylphosphine) palladium (II) (Pd $Cl_2(PPh_3)_2$).

The other type of compound which can be used is a palladium imidazole complex. Imidazole ($C_3N_2H_4$) is a five member ring structure having two nitrogen atoms in the ring. Its structure as well as that of substituted imidazoles are well known and are disclosed in U.S. Pat. No. 6,127,574 which is incorporated by reference in its entirety. Substitution occurs by replacing one or more of the hydrogens with paraffinic or aromatic groups. Examples of substituted imidazoles include but are not limited to 2-methylimidazole, 2-ethylimidazole and benzimidazole. In the rest of this specification and in the claims, Im, will be used to designate both unsubstituted and substituted imidazoles.

The palladium complex is dissolved in a solvent selected from water, alcohols and mixtures thereof. Examples of alcohols include but are not limited to methanol, ethanol, propanol, etc.

A further component of the homogeneous catalyst of this invention is hydrochloric acid (HCl), which is added in any convenient form but usually in a liquid form. The amount of HCl present can range from about 1 to about 500 mol. % and preferably from about 5 to about 200 mol. % of the catalyst. Further, the palladium compound is present in an amount from about 0.01 to about 50 wt. % of the catalyst.

The catalyst described above is used in the carbonylation of olefins to oxygenated products. The oxygenated products can be ketones, aldehydes, alcohols or carboxylic acids with carboxylic acids and alcohols being preferred. Olefins which can be used include linear or branched olefins and internal or terminal, i.e. alpha olefins. The olefin can also be a side chain of a cyclic compound with the cyclic portion being either saturated or aromatic. Regardless of which type of olefin is used it is preferred to use an olefin having 5 or more carbon atoms.

Any source of olefins can be used, but usually olefins are produced by the dehydrogenation of paraffins. Dehydrogenation is a well known reaction and process which involves contacting a paraffin stream with a bed of a solid dehydrogenation catalyst at dehydrogenation conditions to convert at least a portion of the paraffins to olefins. Specifics on dehydrogenation processes can be found in the art, see for example U.S. Pat. No. 6,646,159 B2 and references therein. Other processes can be used to produce the desired olefins. One such process is the oligomerization of small olefins such as ethylene, propylene or butene or other sequential reactions which produce aliphatic alkenes. For instance, the production of butane oligomers from Fischer-Tropsch olefins is described in U.S. Pat. No. 5,994,601 and from field butanes in U.S. Pat. No. 5,998,685. The production of linear olefins by oligomerization is also described in U.S. Pat. No. 4,689,437 and U.S. Pat. No. 4,716,138 which are incorporated herein for their teaching regarding this technology.

The olefin feedstream will usually not be one pure olefin but will be a mixture of olefins and/or a mixture of isomers. For instance, a preferred source of olefins is the dehydrogenation of paraffinic hydrocarbons obtained from petroleum by adsorptive separation from a stream of the appropriate molecular weight hydrocarbons. This is commonly done in the production of linear alkyl benzene (LAB) used in the production of detergents. Paraffins having a range of carbon numbers, such as $C_9$ to $C_{12}$, $C_{11}$ to $C_{14}$ or $C_{10}$ to $C_{13}$ paraffins, can be extracted from a hydrotreated kerosene fraction and charged to a dehydrogenation zone. The selectivity of the adsorption zone may be controlled by choice of adsorbents and operational technique to provide recovered paraffins which are either straight chain paraffins or a mixture of straight chain and slightly branched paraffins such as monomethyl paraffins.

Alternatively, straight chain paraffins recovered by extraction can be fed to a skeletal isomerization zone in which the straight chain paraffins are converted into isoparaffins with various degrees of branching. The desired structure for the feed paraffin is set by the desired structure of the intended product oxygenate. The adsorptive recovery of the paraffins and any subsequent isomerization steps are therefore also set by this preference. The isomerization steps may include selective adsorptive separation steps which separate the effluent of an isomerization reactor into product and recycle fractions. The feed paraffins may be chosen from such representative compounds as heptane, n-octane, n-nonane, 2-methyl nonane, 3-methyl nonane, 2,3-dimethyl pentane, 2,3,6-trimethyl heptane, 2-methyl 3-propyl decane, etc.

The effluent of a paraffin dehydrogenation zone will normally contain a small amount of byproducts including aliphatic diolefins and aromatic hydrocarbons. While the conversion of diolefins into acceptable di-oxygenates, e.g. di-acids in the carbonylation zone or into unsaturated oxygenates, e.g. acids are alternative embodiments of the subject process, it is presently preferred to remove both diolefins and aromatics from the effluent of the dehydrogenation zone prior to its passage into the carbonylation reaction zone in order to produce high purity saturated oxygenates, e.g. aliphatic acids. Aromatic hydrocarbons are relatively unaffected by the carbonylation reaction and would build up in a recycle stream if not otherwise removed as via a drag stream. Unfortunately, drag streams also remove desired material and therefore add to the cost of the process. It is therefore preferred to remove the diolefinic hydrocarbons from the feed by selective hydrogenation and to then remove the aromatic hydrocarbons by adsorption. These steps may be performed as described in U.S. Pat. No. 5,300,715. The removal of diolefinic hydrocarbons may not be necessary if the products formed from them in the carbonylation reaction are acceptable or desirable products of the process or if the specific diolefins do not react twice with the carbon monoxide.

Although not critical, usually the olefins are dissolved in an organic solvent. General classes of solvents which can be used include without limitation paraffins, ketones and monocyclic aromatic hydrocarbons. It is preferred that the ketones contain 7 or less carbon atoms. Non-limiting examples include toluene, xylenes, methyl ethyl ketone, methyl isobutyl ketone, undecane, acetone, etc. Acetone and o-xylene are especially preferred solvents.

Regardless of the source and specific composition of the olefinic feedstream with or without a solvent, it is flowed to a carbonylation reaction zone where it is contacted with carbon monoxide, a hydroxyl source and the homogeneous carbonylation catalyst described above at carbonylation conditions. Carbonylation conditions include a temperature of about 25 to 200° C., preferably from 100 to 170° C., and a pressure as required to maintain at least a portion (greater than 50 mole %) of the feed hydrocarbon present as a liquid. Significantly elevated pressures on the order of about 2,000 to 20,000 kPa (20 to 200 bar) are often employed, with the subject carbonylation reaction zone preferably being operated at a pressure of about 6,000 to about 10,000 kPa (60 to 100 bar). The pressure is not believed to have a significant effect on the performance of the process other than by its impact on the solubility of the carbon monoxide in the liquid phases. Some catalysts are known to be sensitive to changes in pressure and it is therefore preferred to minimize pressure changes within the process. Specifically, it is preferred that no significant reduction in pressure occur while a significant amount of catalyst is present.

The water or alcohol, e.g. methanol which act as the solvent for the homogeneous catalyst also act as the source of hydroxyls. Whether water or an alcohol such as methanol is used depends on the desired product. When water is used, the final product is an acid while when an alcohol is used the final product is an ester.

The concentration of carbon monoxide in the reaction zone is more difficult to specify due to the tendency of the CO to be concentrated in the gas phase, from which it transfers to the liquid phase. The molar ratio of carbon monoxide to feed olefin in the total contents of the reaction zone is preferably within the broad range of from about 1:1 to about 10,000:1. More preferably this ratio is in the range of from about 10:1 to about 10,000:1. The carbon monoxide concentration can also be measured in terms of pressure, with a carbon monoxide partial pressure of about 8 MPa being preferred.

Although a number of different types of reactors can be used to carry out the present process, a loop-venturi reactor is preferred. These reactors are described in a paper *Loop Venturi Reactor—A Feasible Alternative to Stirred Tank Reactors?* By L. van Dierendonck et al, *Ind. Eng. Chem. Res.* 1998, 37, 734-738.

It is preferred that the entire olefin containing feedstream is passed into a single carbonylation reaction zone. However, this reaction zone may employ more than one reactor in series flow to increase per pass conversion or increase selectivity and reduce overall reactor volume. The two reactors may differ in reaction conditions, carbon monoxide concentration, catalyst or solvent which is employed. Further, the addition of a co-reactant, either water or carbon monoxide may be staged within a single reactor or between sequential reactors. A further process variant comprises the addition of different co-reactants in the different reactors.

Unreactive compounds and by-products may accumulate in the process. It is therefore preferred to continuously remove small portions of the vapor and bottom liquid from the reaction zone contents as drag streams. These streams can be processed to recover compounds which may be returned to the reaction zone or totally removed from the process. Alternatively the drag streams may be passed through purification zones, such as an adsorption, stripping or flash zone, which will reduce the concentration of one or more components of the drag stream and then the entire purified drag stream may be returned to the process. A drag stream and corresponding makeup stream may be needed to maintain the activity of the catalyst. It is believed a palladium-phosphine type catalyst which has been deactivated, as by depressurization, may be regenerable. A regeneration method for catalysts of this type is described in U.S. Pat. No. 3,928,231, which is incorporated herein for this teaching.

An effluent stream from the reactor containing product, residual olefin and solvent is separated via one or more fractionator to give a purified product which is collected.

The following examples are set forth in order to more fully illustrate the invention. It is understood that the examples are only by way of illustration and are not intended as an undue limitation on the broad scope of the invention as set forth in the appended claims.

EXAMPLE 1

In a high pressure reactor, there were mixed: 1 ml of $C_{13}$-$C_{16}$ olefins; 28 mg of $PdCl_2$ $(PPh_3)_2$; 1 ml of $H_2O$; 10 ml of acetone. The pressure and amount of HCl was varied and the mixture reacted at 100° C. for 3 hours at which point the mixture was analyzed for total conversion (%) of the olefins, yield (%) to acids and selectivity (%) to acids. Results from these runs are presented in Table 1.

TABLE 1

Effect of HCl and Pressure on Carbonylation of Olefins

| Run # | Pressure (kPa) | HCl mol. % | Olefin Conversion (%) | Acid Yield (%) | Acid Selectivity (%) |
|---|---|---|---|---|---|
| 1 | 5,000 | 20 | 40.3 | 38.5 | 95.5 |
| 2 | 5,000 | 100 | 80.5 | 73.5 | 94.0 |
| 3 | 5,000 | 200 | 85.7 | 82.5 | 96.3 |
| 4 | 2,000 | 200 | 54.5 | 52.0 | 95.4 |

As a comparison a $C_{10}$-$C_{13}$ olefin feedstream and a pure dodecene-1 feed where tested as follows:

1) $C_{10}$-$C_{13}$ (~10% remainder paraffins)–28 ml, acetone–28 ml, $H_2O$–2.25 ml, $PdCl_2(PPh_3)_2$–0.1 g; HCOOH–6.75 ml and LiI–1.31 g and
2) Dodecene-1 5.6 ml, $H_2O$–2.25 ml, $PdCl_2$ $(PPh_3)_2$–25 mg, HCOOH–6.75 ml, acetone–18 ml, LiI–1.31 g.

Both mixtures were reacted at 10,000 kPa and 150° C. and the results are presented in Table 2.

TABLE 2

Reactivity Using Carbonylation Cocatalyst

| Olefin Feed | Olefin Conversion (%) | Acid Yield (%) | Acid Selectivity (%) |
|---|---|---|---|
| $C_{10}$-$C_{13}$ | 93.5 | 90.8 | 97.1 |
| Dodecene-1 | 92.4 | 83.8 | 90.7 |

Comparing the results in Table 2 versus Table 1, it is observed that surprisingly one can eliminate the formic acid and lithium iodine co-catalyst and replace them with milder HCl and achieve comparable activity and selectivity.

EXAMPLE 2

The effect of solvent is shown by the results in Table 3. The initial mixture and reaction conditions were: $C_{10}$-$C_{13}$ olefins (1 ml, 4 mmol); $PdCl_2$ $(PPh_3)_2$ (28 mg, 1%); $H_2O$ (1 ml, 55 mmol); solvent (10 ml); reaction time (3 hr); pressure (20 bar); temperature (100° C.).

TABLE 3

Effect of Solvent on Olefin Carbonylation

| Solvent | Conversion (%) | Yield (%) | Selectivity (%) |
|---|---|---|---|
| acetone + 10% HCl | 23.1 | 22.0 | 95.2 |
| acetic acid | 6.2 | 5.8 | 93.5 |
| formic acid | 3.8 | 3.4 | 89.5 |

EXAMPLE 3

The effect of pressure is shown by the results in Table 4. The initial mixture and reaction conditions were: $C_{10}$-$C_{13}$ olefins (1 ml, 4 mmol); $PdCl_2(PPh_3)_2$ (28 mg, 1%); $H_2O$ (1 ml, 55 mmol); acetone (10 ml); HCl (0.07 ml, 20 mole %); temperature (130° C.); time (3 hr).

TABLE 4

Effect of Pressure on Olefin Carbonylation

| Pressure (kPa) | Conversion (%) | Yield (%) | Selectivity (%) |
|---|---|---|---|
| 2,000 | 12.1 | 11.7 | 96.7 |
| 5,000 | 26.0 | 23.6 | 90.8 |
| 10,000* | 36.3 | 35.3 | 97.2 |

*Reaction temperature was 100° C.

EXAMPLE 4

The effect of temperature is shown by the results in Table 5. The initial mixture concentrations and reaction conditions were:

$C_{10}$-$C_{13}$ olefins (1 ml, 4 mmol); $PdCl_2(PPh_3)_2$ (28 mg, 1%); $H_2O$ (1 ml, 55 mmol); acetone (10 ml); HCl (0.07 ml, 20 mole %); time (3 hr); pressure (50 bar)

TABLE 5

Effect of Temperature on Olefin Carbonylation

| Temperature (° C.) | Conversion (%) | Yield (%) | Selectivity (%) |
|---|---|---|---|
| 80 | 16.0 | 15.2 | 95.0 |
| 90 | 31.2 | 29.2 | 93.6 |
| 100 | 40.3 | 38.5 | 95.5 |
| 130 | 26.0 | 23.6 | 90.8 |

What is claimed is:

1. An olefin carbonylation process comprising contacting a feedstream comprising a mixture of paraffinic olefinic hydrocarbons with carbon monoxide, and a homogeneous catalyst at carbonylation conditions, thereby converting at least a portion of the olefinic hydrocarbons to oxygenated products and where the homogeneous catalyst consists essentially of a palladium compound having the empirical formula $PdIm_4Cl_2$ where Im is imidazole or a substituted imidazole, HCl and a solvent selected from the group consisting of water, alcohols and mixtures thereof.

2. The process of claim 1 where the palladium compound is present in an amount from about 0.01 to about 50 wt. % of the catalyst.

3. The process of claim 1 where the feedstream is dissolved in a solvent selected from the group consisting of paraffins, ketones and monocyclic aromatic hydrocarbons.

4. The process of claim 3 where the solvent is selected from the group consisting of undecane, acetone, xylenes and toluene.

5. The process of claim 1 where the HCl is present in an amount from about 1 to about 500 mole % of the catalyst.

6. The process of claim 1 where the carbon monoxide is present in an amount from about 1:1 to about 10,000:1 carbon monoxide to olefin molar ratio.

7. The process of claim 1 where the carbonylation conditions include a temperature of about 25° C. to about 200° C. and a pressure of about 2,000 kPa to about 20,000 kPa.

8. The process of claim 1 where the oxygenated product is a carboxylic acid.

9. The process of claim 1 where the alcohol is selected from the group consisting of methanol, ethanol, propanol and mixtures thereof.

* * * * *